(12) United States Patent
Ono et al.

(10) Patent No.: US 6,468,257 B1
(45) Date of Patent: Oct. 22, 2002

(54) DISPOSABLE BODY FLUIDS ABSORBENT ARTICLE

(75) Inventors: Yoshio Ono; Katsumi Mizutani; Akiyoshi Kinoshita, all of Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 48 days.

(21) Appl. No.: 09/715,884

(22) Filed: Nov. 17, 2000

(30) Foreign Application Priority Data

Nov. 19, 1999 (JP) .......................................... 11-330581

(51) Int. Cl.[7] ............................................... A61F 13/15
(52) U.S. Cl. .................... 604/391; 604/385.01
(58) Field of Search ..................... 604/385.02, 385.04, 604/385.21, 385.201, 385.23, 385.24, 385.25, 385.26, 385.27, 385.28, 386, 387, 391, 395

(56) References Cited

U.S. PATENT DOCUMENTS 4,743,245 A * 5/1988 Lassen et al.
4,834,737 A * 5/1989 Khan
4,955,880 A * 9/1990 Rodriguez
5,069,672 A * 12/1991 Wippler et al.
5,108,385 A * 4/1992 Snyder
5,207,662 A * 5/1993 James
5,261,901 A * 11/1993 Guay
5,545,159 A * 8/1996 Lancaster et al.
6,312,420 B1 * 11/2001 Sasaki et al.

FOREIGN PATENT DOCUMENTS

CH        306 502 A    4/1955
DE        662 884 C    6/1938

OTHER PUBLICATIONS

Copy of European Search Report dated Apr. 20, 2001.

* cited by examiner

*Primary Examiner*—Jeanette Chapman
(74) *Attorney, Agent, or Firm*—Baker & Daniels (57) ABSTRACT

A disposable body fluids absorbent article that includes a fastener member which is used to fasten the article to an undergarment. The fastener member is attached the rear surface of the article so that respective ends of the member may occupy respective corners of the article.

7 Claims, 8 Drawing Sheets

DISPOSABLE BODY FLUIDS ABSORBENT ARTICLE

BACKGROUND OF THE INVENTION

This invention relates to a disposable body fluids absorbent article such as a urine holding pad or a sanitary napkin and more particularly to such an article having fastener means by which the article is fastened to an undergarment.

It is well known to provide a sanitary article on its bottom surface with fastener means by which the article is fastened to an undergarment such as a diaper or shorts so that a top surface of the article may be reliably placed against a desired region of the wearer's body. As the fastener means for this purpose, any one of hook and loop members constituting together a so-called mechanical fastener, adhesive or double bond tape has usually been used. For example, the sanitary article in the form of a urine holding pad has already been proposed which is adapted to be detachably fastened to cloth defining the inner surface of the diaper by the fastener means in the form of the hook member. The pad usually comprises a laminated structure consisting of a liquid-pervious topsheet, a liquid-impervious backsheet and a liquid-absorbent core disposed between these two sheets. In many cases, the pad is provided in its transversely middle zone.

With such urine holding pad of prior art, if the pad is moved together with the core having a relatively high rigidity after the pad has been fastened to the diaper and this movement tends to separate a peripheral edge of the pad from the inner surface of the diaper, the movement may affect also the hook member via the core and readily separate the hook member from the diaper.

SUMMARY OF THE INVENTION

It is an object of this invention to provide a disposable body fluids absorbent article fastener means such as member that is reliably resistant to unintentional separation from all undergarment during actual use of the article.

According to this invention, there is provided a disposable body fluids absorbent article comprising a liquid-pervious topsheet; a liquid-impervious backsheet; a liquid-absorbent core disposed therebetween; and the backsheet being provided with fastening members adapted to be anchored on an inner surface of an undergarment.

The article further comprises having a longitudinal direction and a transverse direction orthogonal to the longitudinal direction; the core being contoured by a pair of transversely opposite side edges extending longitudinally parallel to each other, a pair of longitudinally opposite terminal edges circumferentially extending parallel to each other and corners defined by oblique edges each extending between the side edge and the associated terminal edge of the pad; and the fastener members lie on a rear side of the core with interposition of the backsheet and, at the respective corners, are spaced from any one of the terminal edges and the oblique edges by 0~20 mm inwardly of the core in the longitudinal direction and spaced from any one of the side edges and the oblique edges by 0~40 mm inwardly of the core in the transverse direction.

The article according to this invention includes the sheet-like fasteners occupying the corners of this article to resist separation of these corners from the diaper cover during use. This article is configured to be tapered toward its longitudinally opposite terminal edges and this unique configuration facilitates the pad to be inserted into the individual packaging envelope. The fasteners increase a rigidity of the pad in the vicinity of the these terminal edges and thereby further facilitate insertion of the pad into the individual packaging envelope.

DETAILED DESCRIPTION OF THE PREFERRED EMBODIMENTS

Details of a disposable body fluid absorbent article according to this invention will be more fully understood from the description given hereunder with reference to the accompanying drawings.

Figure 1:
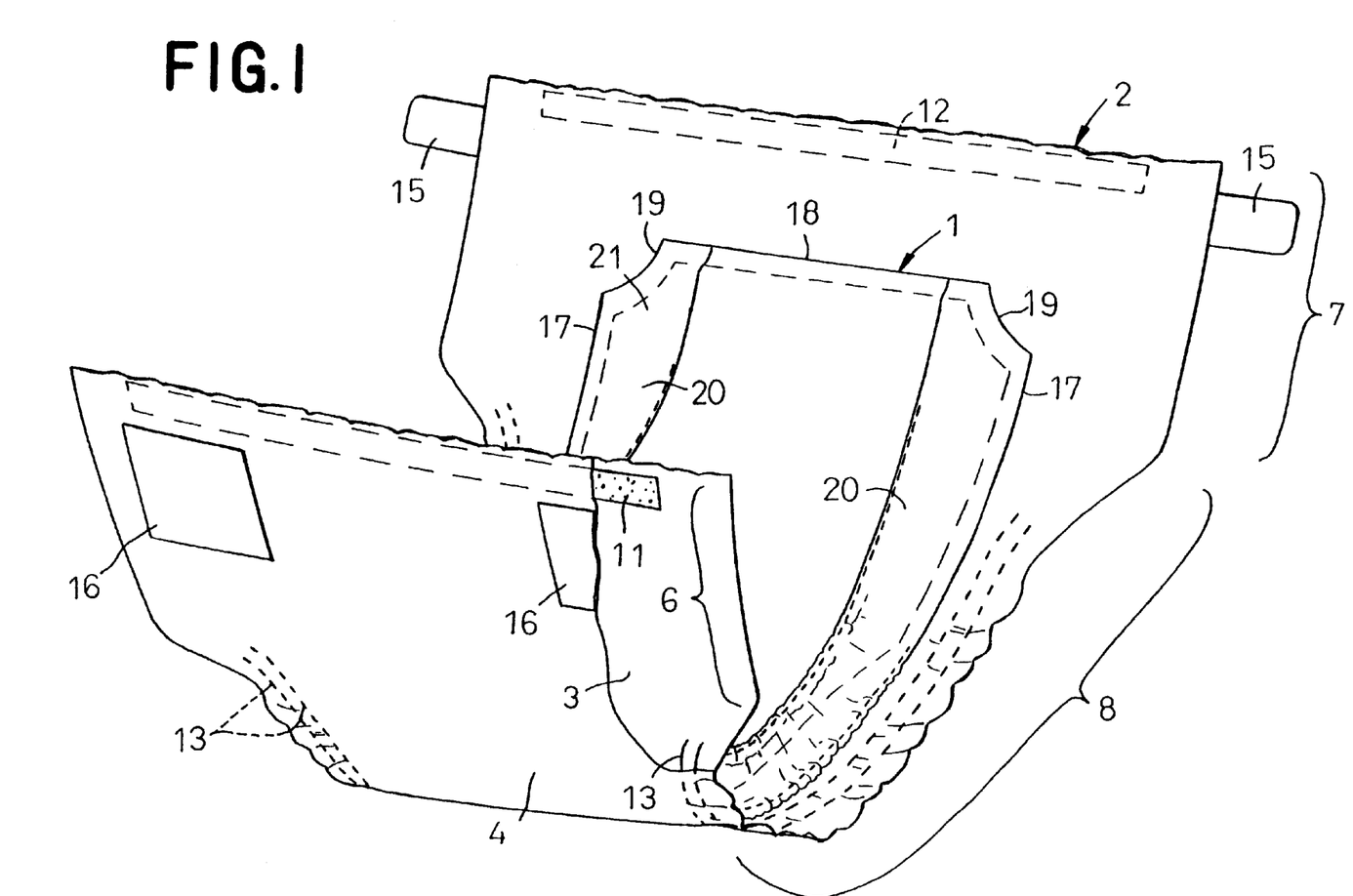
FIG. 1 is a perspective view showing a diaper cover to which a disposable body fluids absorbent article according to this invention has been attached.

FIG. 1 shows a urine holding pad 1 as one embodiment of a disposable body fluids absorbent article as fastened to a diaper cover 2 as one embodiment of an undergarment. The diaper cover 2 comprises an inner sheet 3 made of a nonwoven fabric and an outer sheet 4 made of a plastic film placed upon the inner sheet 3 to configure a front waist region 6, a rear waist region 7 and a crotch region 8 extending between these two waist regions 6, 7. Front and rear terminal edges of the front and rear waist regions 6, 7 respectively, are provided with waist-hole elastic members 11, 12 circumferentially extending between the inner and outer sheets 3, 4 and secured under tension to the inner surface of at least one of the inner and outer sheets 3, 4. Along transversely opposite side edges of the crotch region 8, leg-hole elastic members 13 extend between the inner and outer sheets 3, 4 and secured under tension to the inner surface of at least one of these inner and outer sheets 3, 4. The rear waist region 7 is provided with a pair of tape fasteners 15 extending outward from transversely opposite side edges of the waist region 7, respectively. Each of the fasteners 15 is a hook member adapted to cooperate with a loop member to complete a so-called mechanical fastener. Being adopted for the diaper cover 2, the hook members 15 are intended to be anchored on the loop member attached to the outer sheet 4 of the front waist region 6 in the form of a strip of target tape 16.

The urine holding pad 1 is detachably fastened to the inner side of the diaper cover 2 and contoured by a pair of transversely opposite side edges extending longitudinally parallel to each other across the crotch region 8 into the front and rear waist regions 6, 7, a pair of front and rear terminal edges 18 circumferentially extending parallel to each other (See FIGS. 1 and 2) and four oblique edges 19 each extending between a pair of adjacent ends of the front or rear terminal edge 18 and the associated side edge 17 to define each corner 21 of the pad 1. Spaced from the respective side edges 17, a pair of barrier flaps 20 extending parallel to the side edges 17 between the pair of terminal edges 18.

Figure 2:
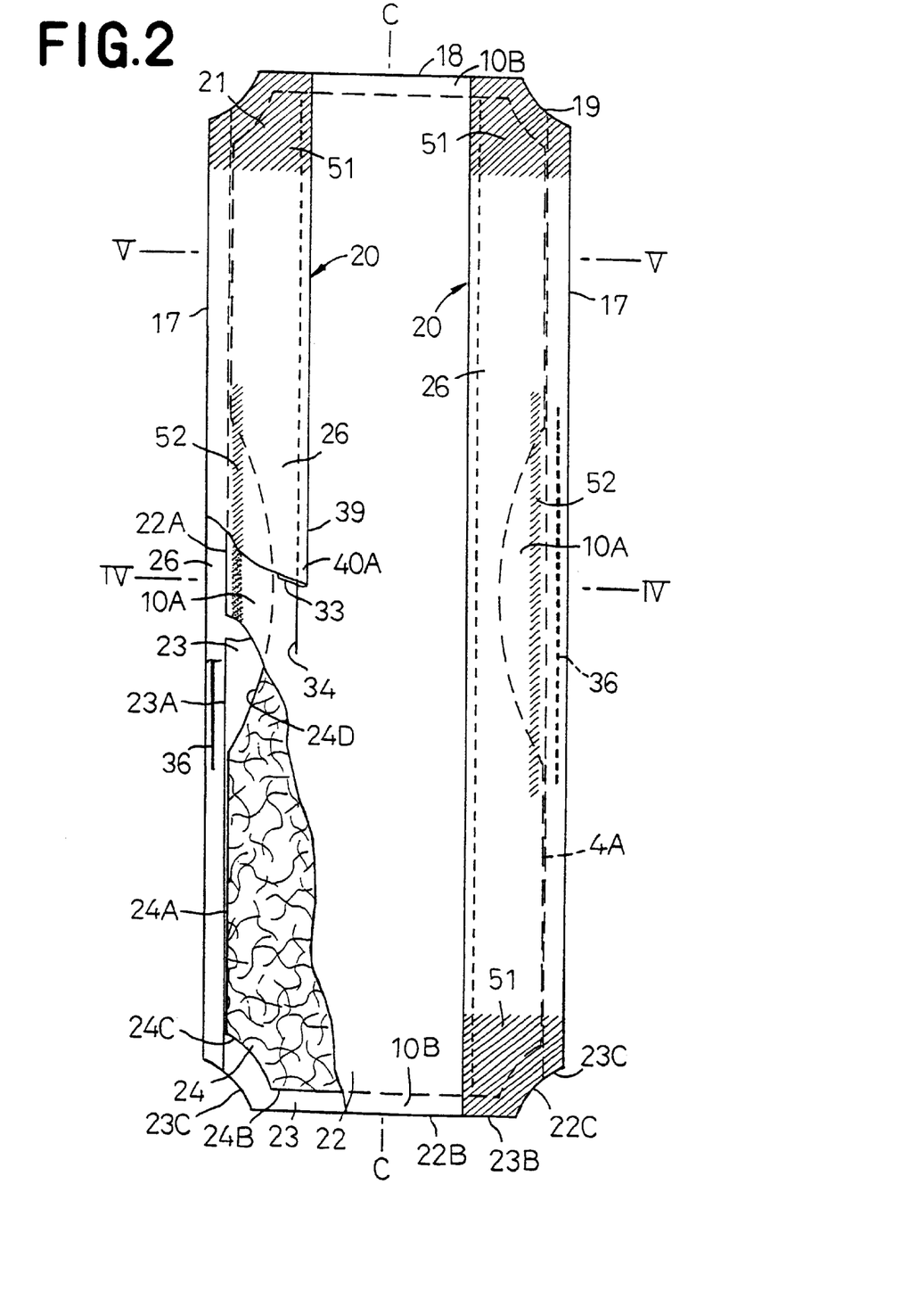
FIG. 2 is a front view showing the partially cutaway article.
Figure 3:
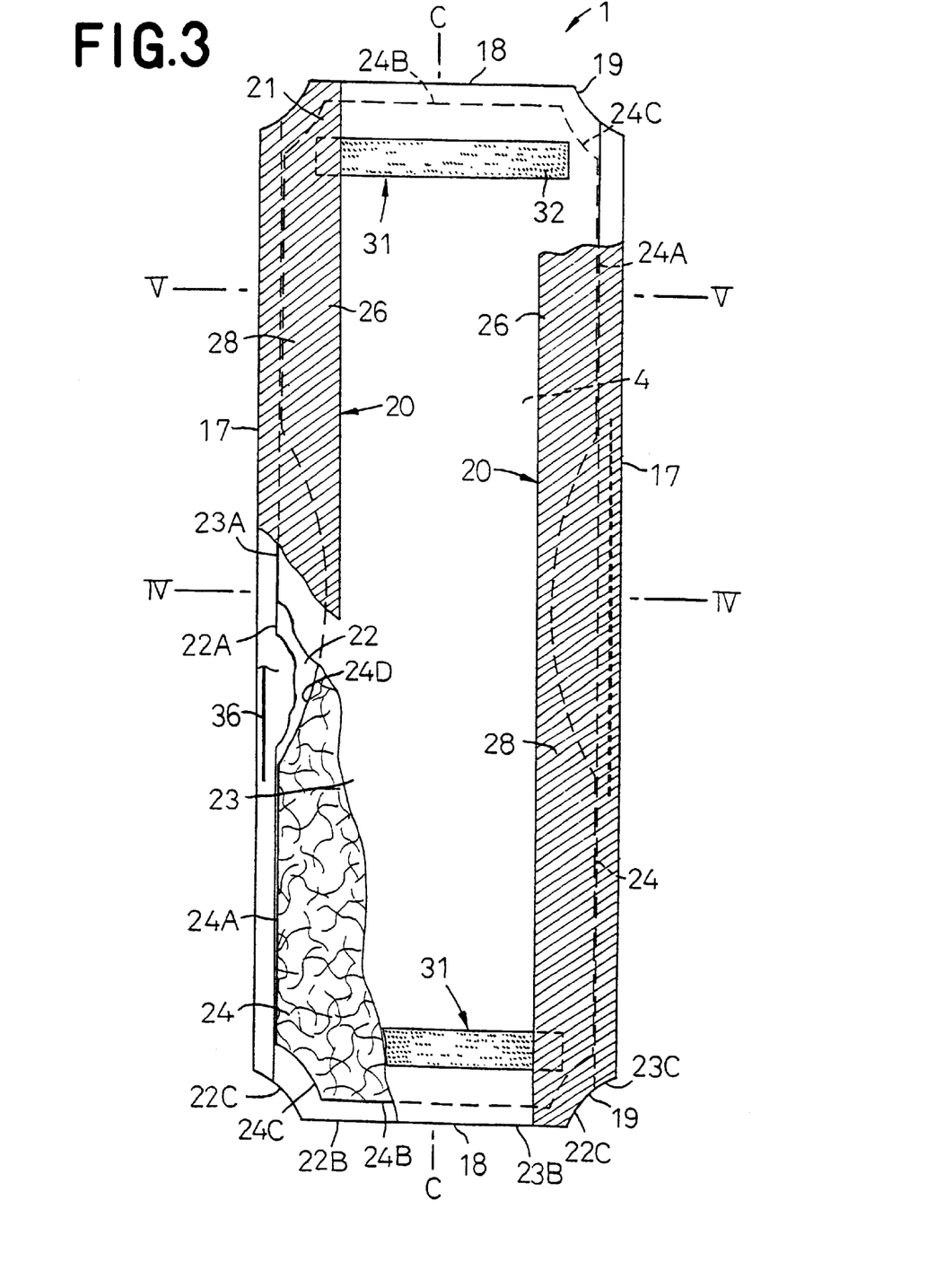
FIG. 3 is a rear view showing the partially cutaway article.
Figure 4:
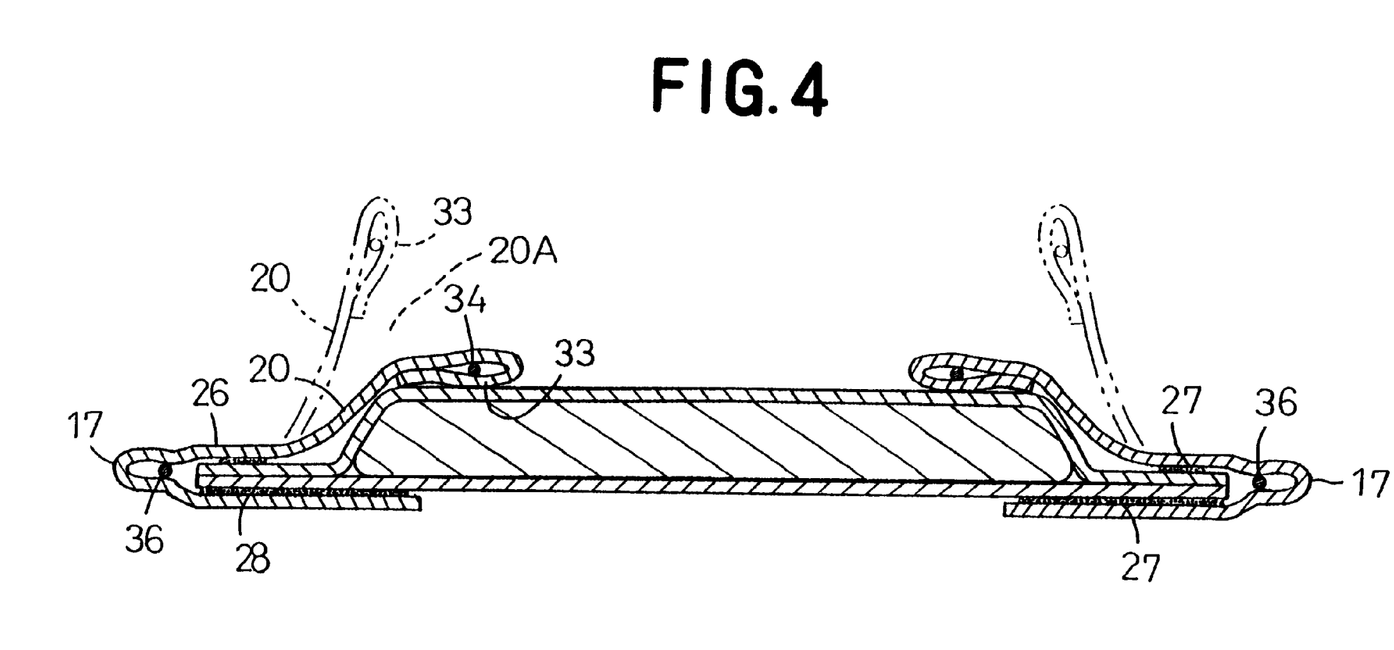
FIG. 4 is a sectional view taken along line IV—IV in FIG. 2.
Figure 5:
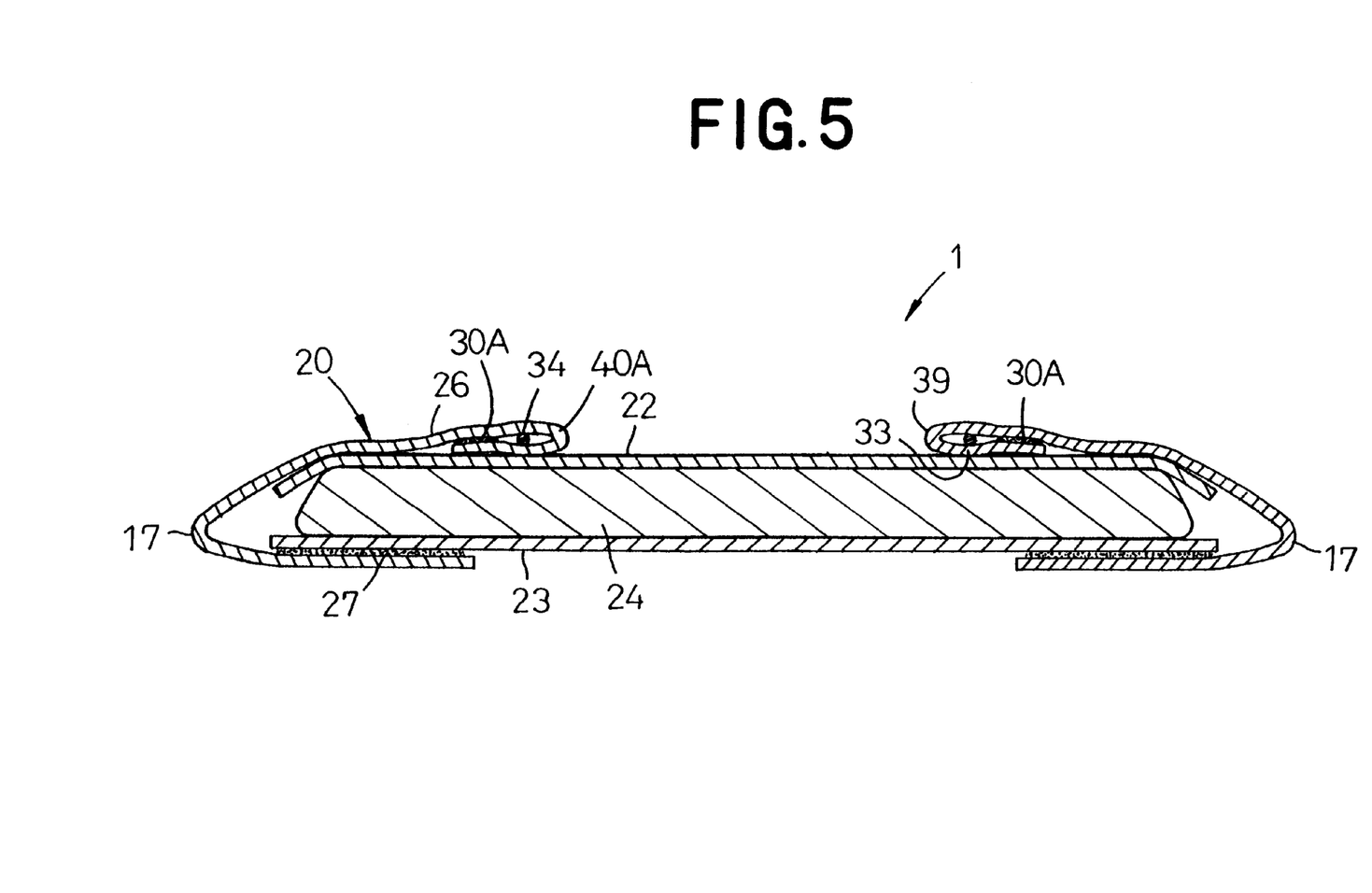
FIG. 5 is a sectional view taken along line V—V in FIG. 2.

FIGS. 2 and 3 are respectively front and rear views showing the article as detached from the diaper cover 2. FIGS. 4 and 5 are sectional views taken along line IV—IV bisecting a length of the pad 1 and along a line V—V in the front view, respectively. The pad 1 comprises a liquid-pervious topsheet 22, a liquid-impervious backsheet 23 and a liquid-absorbent core 24 disposed between these two sheets 22, 23 and is shaped symmetrically about center line C—C bisecting a width of the pad 1. The core 24 is contoured by a pair of transversely opposite side edges 24A extending longitudinally parallel to each other, a pair of longitudinally opposite terminal edges 24B extending transversely parallel to each other, and oblique edges 24C each extending between a pair of adjacent ends of the terminal edge 24B and the associated side edge 24A. The oblique edge 24C slightly curves inwardly of the core 24 so as to reduce a width of the core 24. The side edges 24A curve at their longitudinally middle zones so that the core 24 as a whole may present an hourglass-shape. The topsheet 22 is contoured by transversely opposite rectilinear side edges 22A extending longitudinally along the respective side edges 24A of the core 24, longitudinally opposite terminal edges 22B extending transversely, and oblique edges 22C defined at the respective corners 21 of the pad 1, each oblique edge 22C extending to describe a gentle curve between each pair of adjacent ends of the side edge 22A and the associated terminal edge 22B. The backsheet 23 is substantially identical to the topsheet 22 in shape as well as in size and contoured by transversely opposite rectilinear side edges 23A extending longitudinally along the respective side edges 24A of the core 24, longitudinally opposite terminal edges 23C defined at the respective corners 21 of the pad 1, each oblique edge 23C extending to describe a gentle curve between each pair of ends of the side edge 23A and the associated terminal edge 23B. The top- and backsheets 22, 23 extend outward beyond curved regions 24D of the respective side edges 24A, the longitudinally opposite terminal ends 24B and the oblique edges 24C of the core 24. The top-and backsheets 22, 23 are placed upon and joined to each other over these extensions by means of hot melt adhesive (not shown) to form flaps.

The barrier flaps 20 longitudinally extend along the side edges 17 of the pad 1 between the longitudinally opposite terminal edges 18 including the respective oblique edges 19, each barrier flap 20 being formed using a sheet such as of a nonwoven fabric or a plastic film, preferably using a liquid-impervious sheet and more preferably using a breathable liquid-impervious sheet 26. The portion of the sheet 26 extending on the front surface of the pad 1 is joined to the topsheet 22 at corner join zones 51 and an intermediate join zone 52 (See FIG. 2) as indicated by hatches using hot melt adhesive 27 as shown in FIGS. 2 and 4. The portion of the sheet 26 extending -on the rear surface of the pad 1 is joined to the backsheet 23 at a join zone 28 indicated by hatches using hot melt adhesive 27 (See FIGS. 3 and 4).

The sheet 26 forming the barrier flap 20 is folded back along the side edge 17 onto the front and rear surfaces of the pad 1. The portion of the sheet 26 folded onto the front surface of the pad 1 has its distal marginal region 33 folded back with its inner surface inside and joined to itself with using hot melt adhesive (not shown). The distal marginal region 33 thus folded back wraps a first elastic member 34 extending between the longitudinally opposite terminal edges 24B of the core 24 and secured under tension to the sheet 26 by means of hot melt adhesive (not shown) at least the opposite ends of the first elastic member 34. It is possible to bond the first elastic member 34 to the sheet 26 not only at its opposite ends but also intermittently over its intermediate region defined between the opposite ends. In the vicinity of the side edge 17 of the pad 1, the sheet 26 folded back along the side edge 17 wraps a second elastic member 36 longitudinally extending and secured under tension to the inner surface of the sheet 26 by means of hot melt adhesive (not shown) preferably in an intermittent fashion. The second elastic member 36 is placed opposite to the curved region 24D of the core 24 so that gathers may be generated in the portion of the sheet 26 and preferably also in the portions of the top- and backsheets 22, 23 extending outside the curved region 24D.

Referring now to FIG. 3, there are provided a pair of rectangular fasteners 31 on the rear side of the pad 1 immediately inside the longitudinally opposite terminal edges, respectively. The fasteners 31 serve for detachably fastening the pad 1 to the inner side of the diaper cover 2 and each of these fasteners 31 may be formed by suitable means such as one of a hook member and a loop member constituting together a so-called mechanical fastener or a strip of pressure-sensitive adhesive tape. The fasteners 31 extend transversely of the pad 1 and are attached to the backsheet 23 by means of hot melt adhesive or pressure-sensitive adhesive so that respective lateral ends 32 of the fasteners 31 may lie adjacent the respective corners 21 of the pad 1.

Figure 6A:
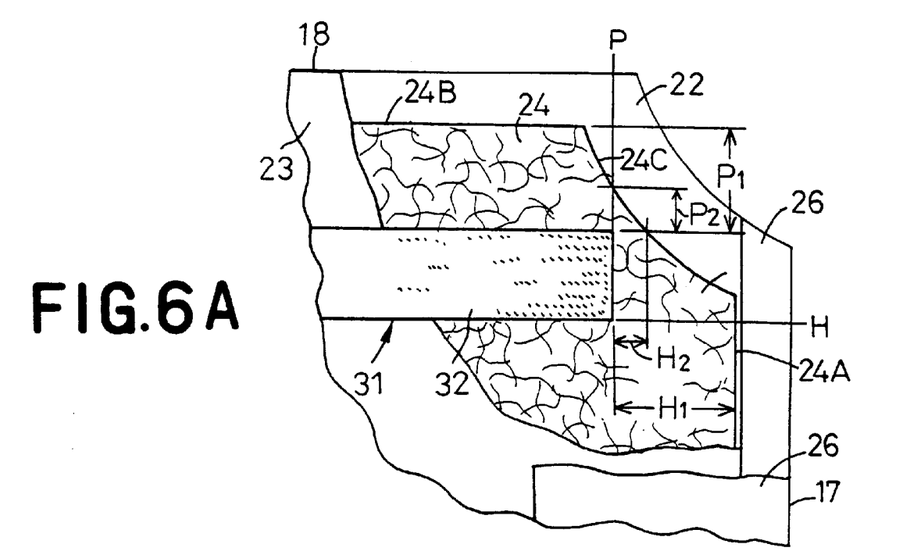
FIG. 6 is a fragmentary view illustrating various manners in which a fastener member may be attached to the article in (a)~(c)
Figure 6B:
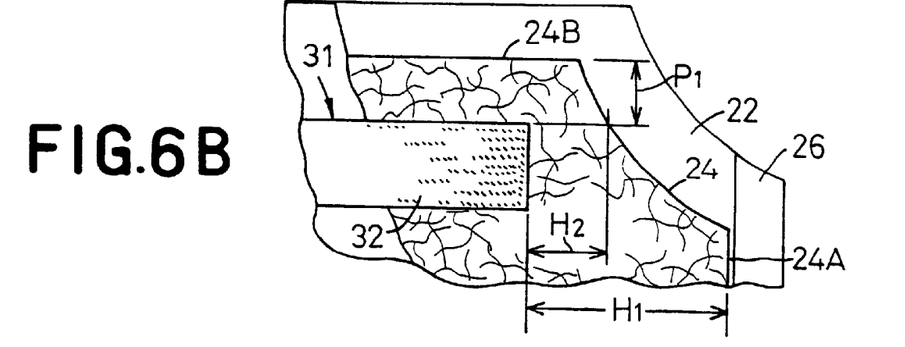
Figure 6C:
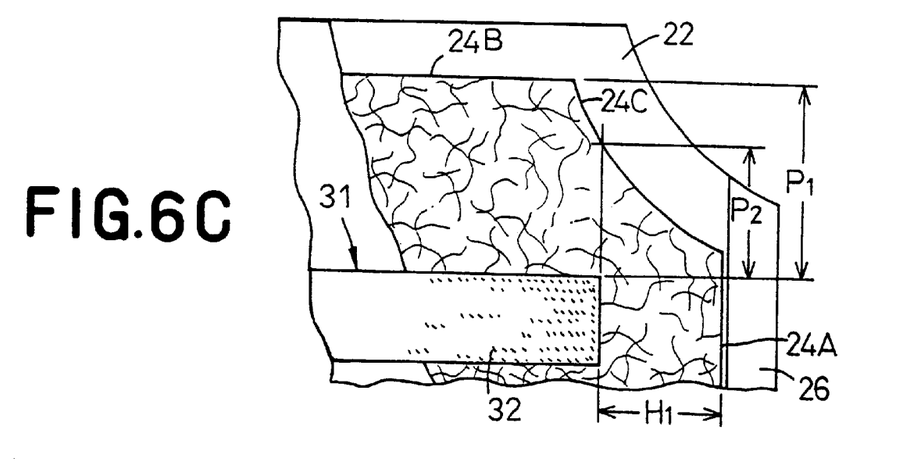

FIG. 6 shows the corner 21 of the partially cutaway, pad 1 in which (a)~(b) illustrate various possible manners of placement of the fastener 31 at the corner 21. In the case of (a), the end 32 of the fastener 31 lies adjacent the oblique edge 24C. The longitudinal minimum distances from the end 24B and the oblique edge 24C of the core 24 to the fastener 31, respectively, as measured along a perpendicular line P extending parallel to the center line C—C (See FIG. 2) bisecting the width of the pad 1 are designated by $P_1$, and $P_2$. The transverse minimum distances from the side edge 24A and the oblique edge 24C to the fastener 31, respectively, as measured along a horizontal line H orthogonal to the center line C—C are designated by $H_1$, and $H_2$. The end 32 of the fastener 31 is attached to the rear surface of the pad 1 so that at least one of $P_1$ and $P_2$ is in a range of 0~20 mm and at least one of $H_1$ and $H_2$ is in a range of 0~40 mm. The fastener 31 shown in (b) has its transverse dimension is smaller than that of the fastener 31 shown in (a) and is attached to the rear surface of the pad 1 so that $P_1$ is in a range of 0~20 mm and at least one of $H_1$ and $H_2$ is in a range of 0~40 mm. The fastener 31 shown in (c) occupies a position lower than that of the fastener 31 shown in (a) and is attached to the pad 1 so that at least one of $P_1$ and $P_2$ is in a range of 0~20 mm and $H_1$ is in a range of 0~40 mm. While it is desirable that the end 32 is not covered with the sheet 26 in order to reliably fix the corner 21 of the pad 1 to the diaper cover 2, the end 32 may be covered with the sheet 26 as shown in FIG. 3 to prevent the corners of the fastener 31 from uncomfortably irritating the wearer's skin.

Figure 7:
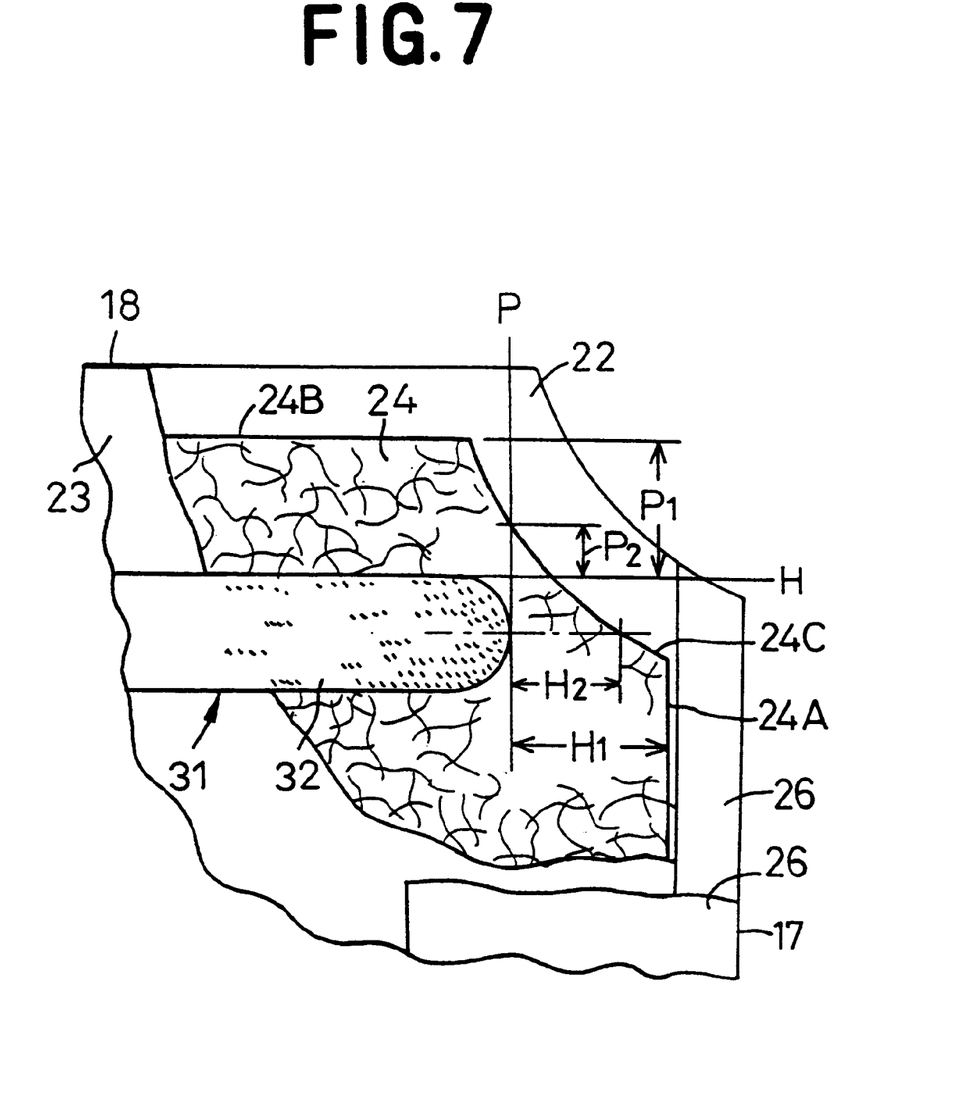
FIG. 7 is a view similar to FIG. 6 illustrating still another manner in which the fastener member may be attached to the article.

FIG. 7 is a view similar to FIG. 6 except that the fastener 31 has a rounded end 32. At least one of the minimum distances $P_1$ and $P_2$ from the terminal edge 24B and the oblique edge 24C of the core 24 to the end 32 of the fastener 31, respectively, as measured along the perpendicular line P is in a range of 0~20 mm. At least one of the minimum distances $H_1$ and $H_2$ from the side edge 24A and oblique edge 24C of the core to the end 32 of the fastener 31, respectively, as measured along the horizontal line H is in a range of 0~40 mm.

Figure 8:
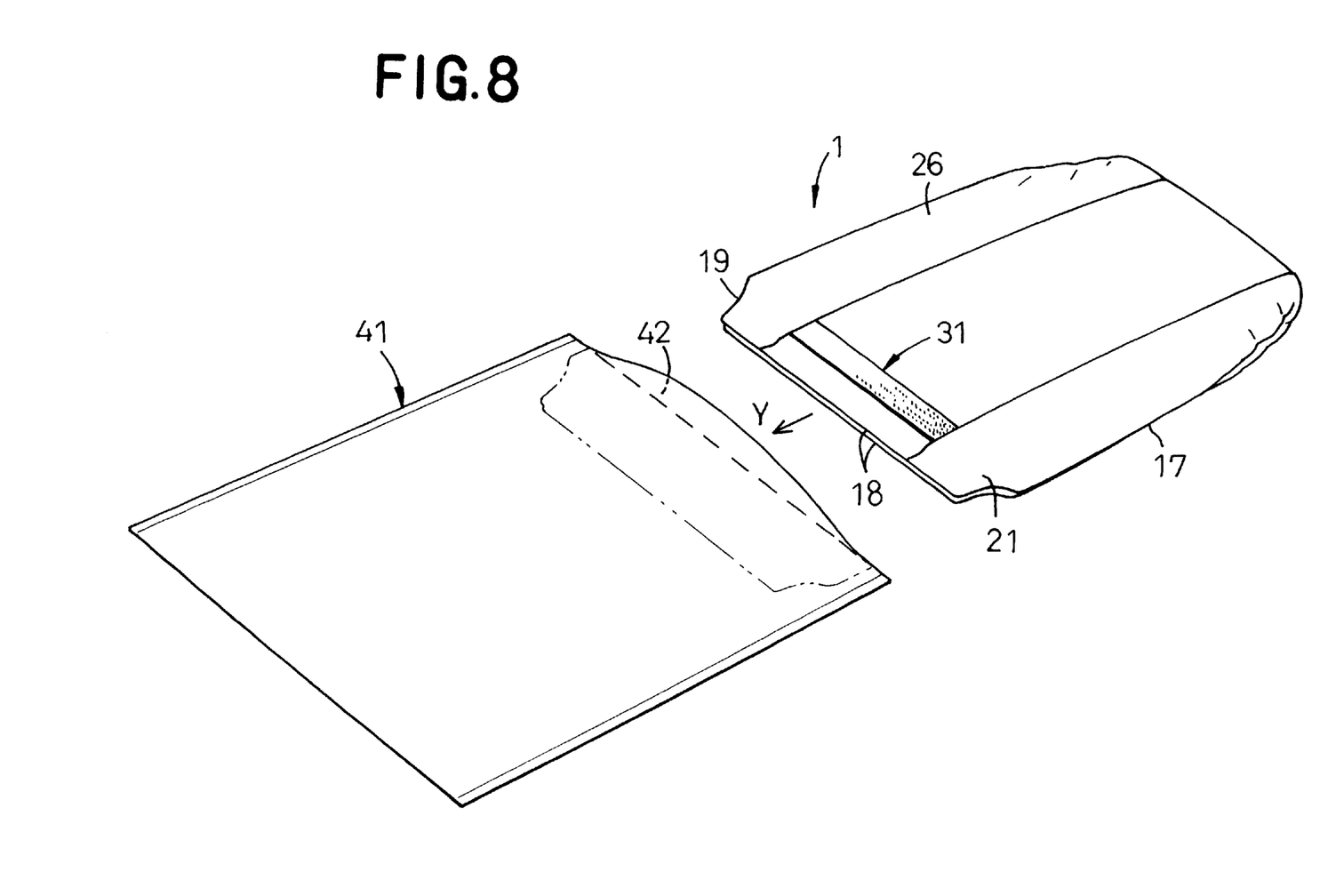
FIG. 8 is a perspective view showing the article together with its individual packaging envelope.

FIG. 8 is a perspective view showing the pad 1 folded in two along center line IV—IV bisecting a length of the pad 1 as immediately before this pad 1 is inserted into its individual packaging envelope 41 in a direction indicated by an arrow Y. As will be apparent from FIGS. 2 and 3, the pad 1 has its width reduced in the vicinity of the terminal edges 18 the forward end of the pad 1 thus folded in two is appropriately tapered. As a result, the pad 1 folded in two can be easily inserted into the individual packaging envelope 41 through an opening of this envelope 41. Additionally, the fastener 31 lies adjacent the terminal edge 24B of the core 24 and contributes to a further increased rigidity of the core 24. This is another factor facilitating the pad 1 to be easily inserted into the individual packaging envelope 41.

With the pad 1 of such an arrangement having been fastened to the diaper cover 2, the fasteners 31 occupy the corners 21 of the pad 1 corresponding to the corners of the core 24 presenting a relatively high rigidity and ensure the corners 21 to be reliably fixed to the diaper cover 2. The corners 21, particularly the rigid corners of the core 24 are not angular and, even if the diaper cover 2 is lifted up along the wearer's body, it is not apprehended that a force tending to separate the corners 21 from the diaper cover 2 might be focused upon the corners 21 and consequently the corners 21 might be easily separated from the diaper cover 2 as the angular corners have been the case. In this way, this pad 1 is free from the trouble that the corners 21 might be easily separated from the diaper cover 2 both in the course of putting the article on the wearer's body and after having been put on the wearer's body.

As the diaper cover 2 is put on the wearer's body and longitudinally curved as seen in FIG. 1, the pad 1 is also curved under contraction of the first and second elastic members 34, 36 of the pad 1. Contraction of the first elastic member 34 causes the barrier flap 20 to rise as indicated by imaginary lines in FIG. 4 and thereby to form a pocket 20A opening inwardly of the pad 1. Contraction of the second elastic member 36 generates gathers in the vicinity of the side edge 17 of the pad 1 and these gathers come in elastic contact with the wearer's leg.

The fastener 31 is already effective to facilitate insertion of the pad 1 into the individual packaging envelope and to ensure the pad 1 to be reliably fixed to the diaper cover 2. To further improve such effect of the fastener 31, the pad 1 assembled integrally with the backsheet 23 preferably has a rigidity at least 3 times higher than that of the backsheet 23 longitudinally and/or transversely of the pad 1. The rigidity is measured in accordance with Clarke Method or Cantilever Method prescribed by JIS (Japanese Industrial Standards) L.1018. Instead of the fastener 31 which is continuous transversely of the pad 1 as in the embodiment illustrated, it is also possible to use the fastener 31 divided in two or more transversely of the pad 1. However, the continuous fastener 31 is relatively efficient to improve the rigidity in the vicinity of the ends 18 of the pad 1.

Within the scope of this invention, it is also possible to adopt the manner in which the fasteners 31 are attached to the pad 1 as illustrated along only one of the longitudinally opposite terminal edges 18 of the pad 1. Such simplification is suitable for the case in which the effect of preventing the pad 1 from being separated from the diaper cover 2 is less important along the other terminal edge 18 than the one terminal edge 18. Bonding of the members may be carried out, instead of using hot melt adhesive, by the other bonding means such as heat-sealing technique. The article for disposal of body fluids according to this invention is useful not only as the illustrated urine holding pad but also as a sanitary napkin, a panty liner or the like.

What is claimed is:

1. A disposable body fluids absorbent article comprising:

a liquid-pervious topsheet;

a liquid-impervious backsheet;

a liquid-absorbent core disposed therebetween;

said backsheet being provided with fastening members adapted to be anchored on an inner surface of an undergarment;

said article having a longitudinal direction and a transverse direction orthogonal to said longitudinal direction;

said core being contoured by a pair of transversely opposite side edges extending longitudinally parallel to each other, a pair of longitudinally opposite terminal edges circumferentially extending parallel to each other and corners defined by oblique edges each extending between the side edge and the associated terminal edge of the pad; and said fastener members lying on a rear side of said core with interposition of said backsheet and, at each said corners, being spaced from any one of said terminal edges and said oblique edges by 0~20 mm inwardly of said core in said longitudinal direction and spaced from any one of said side edges and said oblique edges by 0~40 mm inwardly of said core in said transverse direction.

2. The article according to claim 1, wherein said fastener member is a hook member of a mechanical fastener.

3. The article according to claim 1, wherein said fastener member is a strip of adhesive tape.

4. The article according to claim 1, wherein said fastener member is a single belt-like member extending parallel to at least one of said longitudinally opposite terminal edges between a pair of transversely opposite said corners.

5. The article according to claim 1, wherein flaps are formed outside any one of said side edges, terminal edges and oblique edges.

6. The article according to claim 1, wherein said fastener member and said backsheet are integrally attached to each other and such an assembly of said fastener member and said backsheet has a rigidity 3 times or more higher in at least one of said longitudinal and transverse directions than a rigidity of said backsheet in the corresponding direction.

7. The article according to claim 1, wherein said article is folded back along a center line bisecting a dimension of the article in said longitudinal direction and inserted, in such folded state, into an individual packaging envelope.

* * * * *